United States Patent [19]

Lobos et al.

[11] Patent Number: 5,118,878
[45] Date of Patent: Jun. 2, 1992

[54] METHOD FOR BIODEGRADING AND BIOTRANSFORMING BISPHENOL ALKANES, AND BISPHENOL ALKKYL ALCOHOLS MADE THEREFROM

[75] Inventors: John H. Lobos, Rexford; Terry K. Leib; Tah-Mun Su, both of Schenectady, all of N.Y.

[73] Assignee: General Electric Company, Schenectady, N.Y.

[21] Appl. No.: 691,902

[22] Filed: Apr. 26, 1991

Related U.S. Application Data

[62] Division of Ser. No. 625,381, Dec. 11, 1990, Pat. No. 5,070,017.

[51] Int. Cl.$^5$ .............................................. C07C 33/26
[52] U.S. Cl. .................................. 568/809; 435/170; 435/252.1; 568/715; 568/807; 568/808; 568/811
[58] Field of Search ............... 568/729, 811, 715, 808, 568/722, 817, 809; 435/252.1, 170

[56] References Cited

U.S. PATENT DOCUMENTS 4,133,729  9/1979  King ........................ 568/729

FOREIGN PATENT DOCUMENTS 126895  5/1944  Australia ........................ 568/729
834961  5/1960  United Kingdom ............ 568/729

*Primary Examiner*—Werren B. Lone
*Attorney, Agent, or Firm*—William A. Teoli; James C. Davis, Jr.; William H. Pittman

[57] ABSTRACT

A gram-negative, aerobic, motile, rod-shaped bacterium which is closely related to *Chryseomonas luteola* and *Flavimonas oryzihabitans*, has been found to catalyze the biodegradation and biotransformation of bisphenol alkanes, such as 2,2-bis(4-hydroxyphenyl)-propane or bisphenol A. A variety of bisphenol alkyl alcohols can be made by this procedure.

5 Claims, No Drawings

METHOD FOR BIODEGRADING AND BIOTRANSFORMING BISPHENOL ALKANES, AND BISPHENOL ALKKYL ALCOHOLS MADE THEREFROM

This application is a continuation of U.S. Ser. No. 07/625,381, filed Dec. 11, 1990 U.S. Pat. No. 5,070,017.

BACKGROUND OF THE INVENTION

The present invention relates to a method for biotransforming bisphenol alkanes, such as bisphenol A, to convert these materials to hydroxylated reaction products, such as the corresponding bisphenol alkyl alcohols. The present invention also includes the biodegradation of bisphenol alkanes to carbonyl reaction products, such as aromatic aldehydes, aromatic acids, aromatic ketones and carbon dioxide.

Bisphenol alkanes, such as bisphenol A, are used in the production of plastics at numerous chemical manufacturing sites throughout the world. For example, annual production of bisphenol A exceeded 930M pounds in recent years. As a result, significant quantities of waste containing bisphenol A are generated at these various manufacturing facilities which is discharged into the terrestrial, aquatic and marine environments. According to standard evaluation procedures published by the US Environmental Protection Agency (EPA), bisphenol A was determined to be slightly to moderately toxic to fish and invertebrates. As a result, continuous efforts are being made to determine satisfactory procedures for minimizing the risks of bisphenol alkanes introduced into the environment.

SUMMARY OF THE INVENTION

The present invention is based on the discovery that a certain gram-negative, aerobic, motile, rod-shaped bacterium, which is most closely related to *Chryseomonas luteola* and *Flavimonas orysihabitans*, hereinafter referred to as strain MVI, has been found to catalyze the biodegradation and biotransformation of bisphenol alkanes. Suprisingly, strain MVI also has been found to selectively hydroxylate the aliphatic moiety of the bisphenol alkane resulting in the production of a variety of a trifunctional and tetrafunctional bisphenols which are useful as monomers for making plastics.

STATEMENT OF THE INVENTION

There is provided by the present invention, a method for biodegrading or biotransforming bisphenol alkanes, which comprises treating bisphenol alkanes under aerobic conditions at a pH in the range from 6.0 to 7.0 with an effective amount of a biologically pure culture of the gram-negative, motile, rod-shaped bacterium, NRRL-B-18737 (or strain MVI).

In another aspect of the present invention, there is provided a method for biotransforming particular bisphenol alkanes to bisphenol alkyl alcohols by treating the bisphenol alkanes under aerobic conditions and at a pH in the range from 6.0 to 7.0 with an effective amount of a biologically pure culture of the gram-negative, motile, rod-shaped bacterium, NRRL-B-18737, in an aqueous mineral salts medium at 25°-30° C.

A culture of the bacterial strain MVI used in the practice of the present invention, is on deposit with the U.S. Department of Agriculture as NRRL-B-18737. A progeny of the subject microorganism will be provided by the assignee of this application under the conditions imposed by 37 CFR 1.114 and 35 USC 122 in the event that the Commissioner of Patents and Trademarks determines that an individual is entitled to the same.

Upon issuance of the subject application as a patent, a culture of this strain can be obtained from the permanent collection of the Agricultural Research Culture Collection (NRRL) at the Northern Regional Research Center, U.S. Department of Agriculture, Peoria, Ill., U.S.A.

The taxonomic identification of strain MV1 is found to share features common to *Chryseomonas luteola* and *Flavimonas oryzihabitans*. Colonies of strain MVI were found to be round, smooth, entire and dull with a yellow pigment. Cells were found to be gram-negative rods with 1-2 polar flagella.

| Key Biochemical Characteristics of Strain MV1 | |
| --- | --- |
| Glucose | Acid (A) |
| Fructose | A |
| Mannose | A |
| Xylose | A |
| Mannitol | − |
| MacConkey agar | growth |
| Yellow pigment | + |
| Gluconate oxidation | − |
| Indole | − |
| H$_2$S production | − |
| Oxidase | − |
| Lysine | − |
| Ornithine | − |
| Lecithinase | − |
| Hemolysis | Beta |
| Gram positive | − |
| Gram negative | + |
| Gram variable | − |
| Motile at 37° C. | − |
| Motile at Room Temperature | + |
| Flagella peritrichous | − |
| Flagella lophotrichous | ? |
| Flagella monotrichous | + |
| Flagella lateral | − |
| 4° C. growth | − |
| 25° C. growth | + |
| 30° C. growth | + |
| 37° C. growth | + |
| 41° C. growth | − |
| Pigment diffusible | − |
| Pigment non-diff. | + |
| Pyocyanine produced | − |
| Fluorescein produced | − |
| Melanin pigment produced | − |
| pH 6.0 growth | + |
| 3% NaCl growth | + |
| 6.5% NaCl growth | − |
| Skim milk agar growth | + |
| Aesculin hydrolysis | + |
| Casein hydrolysis | − |
| Starch hydrolysis | + |
| Gelatinase | − |
| Tween 80 hydrolysis | + |
| Simmons citrate growth | + |
| Urease | W |
| Nitrate to nitrite | − |
| Nitrite reduction | − |
| Hydrogen sulfide (TSI) PbAc | + |
| Lysine decarboxylase | − |
| Arginine (Mollers) | − |
| Ornithine decarboxylase | − |
| Phenylalanine deamination | − |
| Phosphatase | + |
| Catalase | + |
| Growth on malonate as SCS | − |
| Tyrosine degradation | W |
| dl-hydroxybutyrate growth | + |
| PHB accumulation | + |
| Deoxyribonuclease | − |
| Growth on 0.05% cetrimide | − |
| Growth on acetate as SCS | + |
| Testosterone deg. | − |

| -continued |
| --- |
| Key Biochemical Characteristics of Strain MV1 |
| 3-Ketolactose — |

Some of the bisphenol alkanes which can be hydroxylated in accordance with the practice of the invention are, for example,

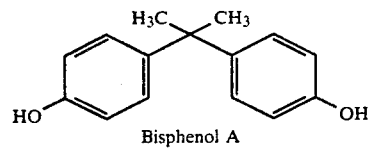
Bisphenol A

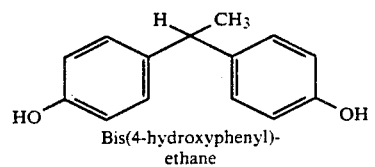
Bis(4-hydroxyphenyl)-ethane

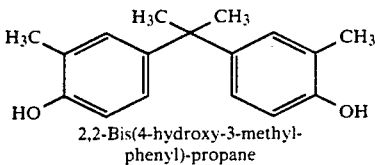
2,2-Bis(4-hydroxy-3-methylphenyl)-propane

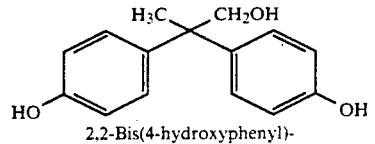
2,2-Bis(4-hydroxyphenyl)-1-propanol

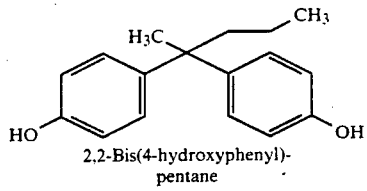
2,2-Bis(4-hydroxyphenyl)-pentane

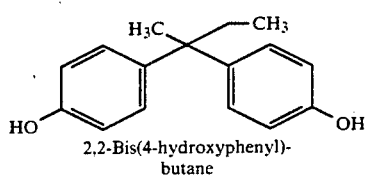
2,2-Bis(4-hydroxyphenyl)-butane

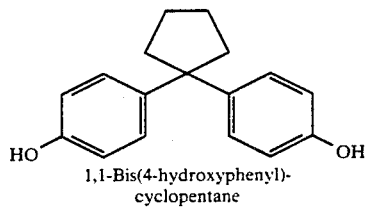
1,1-Bis(4-hydroxyphenyl)-cyclopentane

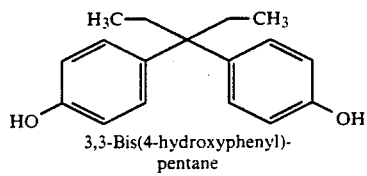
3,3-Bis(4-hydroxyphenyl)-pentane

The biochemical pathway for the biodegradation of bisphenol A by strain MV1 is as follows:

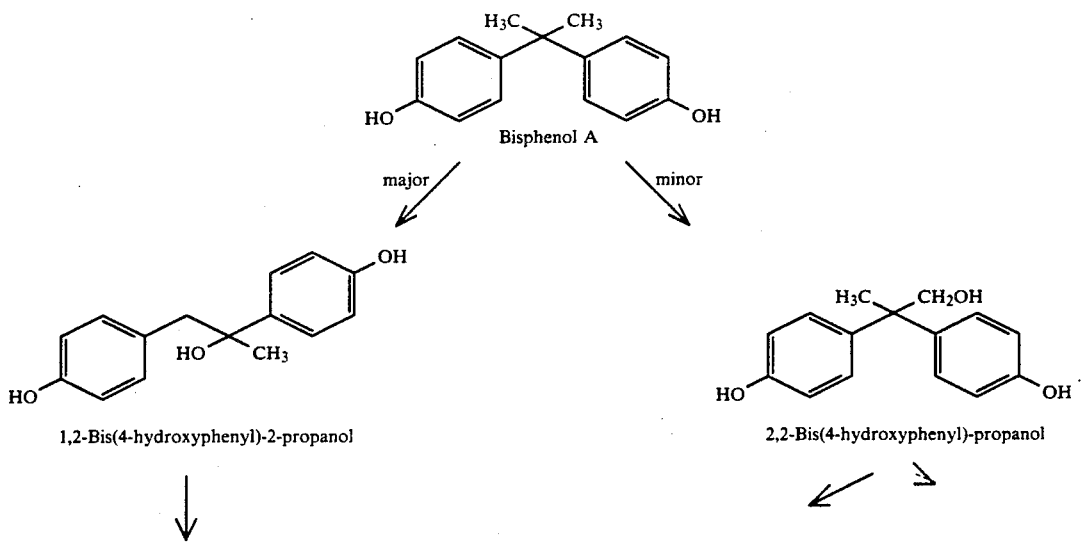

-continued

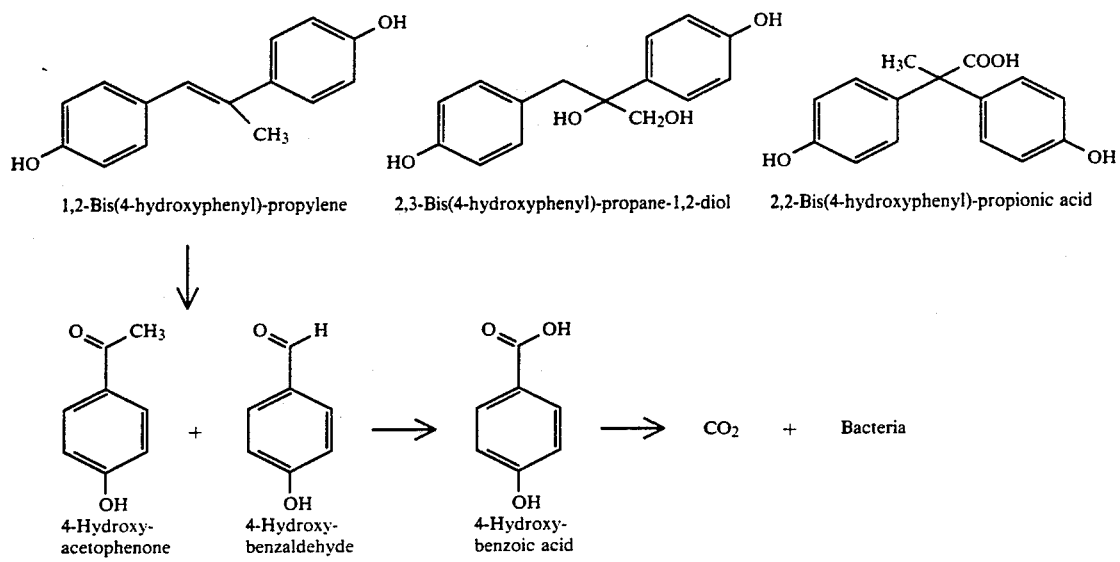

1,2-Bis(4-hydroxyphenyl)-propylene   2,3-Bis(4-hydroxyphenyl)-propane-1,2-diol   2,2-Bis(4-hydroxyphenyl)-propionic acid 4-Hydroxy-acetophenone + 4-Hydroxy-benzaldehyde → 4-Hydroxy-benzoic acid → $CO_2$ + Bacteria In order that those skilled in the art will be better able to practice the present invention, the following examples are given by way of illustration and not by way of limitation. All parts are be weight unless otherwise indicated.

EXAMPLE 1

Ten ml of a sludge containing bisphenol A taken from an industrial waste treatment plant was added to 50 ml of a PAS culture medium containing 100 mg of bisphenol A and 0.005% yeast extract. The PAS culture medium consisted of the following:

|  | g/L | Final conc. g/L medium |
|---|---|---|
| PAS Salts (100X) SALT |  |  |
| $MgSO_4$ | 19.5 g | 0.195 g/L |
| $MnSO_4 \cdot H_2O$ | 5.0 | 0.05 |
| $FeSO_4 \cdot 7H_2O$ | 1.0 | 0.01 |
| $CaCl_2 \cdot 2H_2O$ | 0.3 | 0.03 |
| conc. HCL - 1 ml/L Filter Sterilized |  |  |
| PA Concentrate (20X) |  |  |
| $K_2HPO_4$ | 87.0 g | 4.35 |
| $KH_2PO_4$ | 33.7 | 1.69 |
| $NH_4Cl$ | 52.5 | 2.13 |

*PA added before or after autoclaving, depending on substrate.
ADD 100x PAS salts after autoclaving
*For agar plates, use 15 g purified agar/L of medium.
*Final conc. is 37 mM phosphate, pH = 6.8

The resulting mixture was incubated aerobically under sealed conditions in a rotary shaker-incubator set at 30° C. and 200 RPM. After one week, the bisphenol A particles disappeared from the culture medium. A subculture of the week-old culture was obtained by transferring 2 ml of the grown enrichment culture to 50 ml of PAS medium containing bisphenol A (100 mg) as the carbon source. After another week, a second subculture was obtained by transferring 2 ml of the 1st subculture into another 50 ml PAS medium with bisphenol A. The second subculture grew to an optical density of 2.5 (absorbance at 600 nm, spectronic 20 spectrophotometer) after 48 hours incubation. The subculture was used to study the rate of bisphenol A degradation as a mixed culture via subsequent subcultures.

A sample of the above enriched subculture was then grown on PAS plates utilizing a PAS medium solidified with 1.5% agar which contained fine crystals of bisphenol A dispersed throughout a culture dish. The enriched subculture which was grown on bisphenol A was streaked out on the PAS plates and incubated for 2 weeks. After one week, the growth which resulted did not produce any isolated colonies. However, a clearing of the agar due to the dissolution and degradation of bisphenol A was observed around and under the area where cell growth occurred. Upon restreaking several times on PAS plates containing bisphenol A, isolated colonies were obtained. The isolated colonies were checked for uniformity on a nutritionally-rich medium containing glucose as a carbon and energy source. The colonies which resulted were demonstrated to be uniform and of a single species of bacterium (strain MV1). Poor growth was observed when the bacterial isolates were returned to PAS medium with bisphenol A as the sole carbon source. The strain MV1 had a tendency to lose its ability to grow on bisphenol A at saturating levels when it was cultured on alternate substrates in the absence of bisphenol A for extended periods of time.

A carbon mass balance for strain MV1 grown on bisphenol A was done utilizing a total organic carbon analyzer (Shimadzu, Japan). Strain MV1 was grown in triplicate sealed 120 ml serum bottles containing 20 ml of PAS medium and 0.132 millimoles bisphenol A (equal to 2 millimoles carbon). After inoculation, the serum bottles were pressurized with air to approximately 1.5 atmospheres and incubated at 30° C. on a rotary shaker incubator. Complete degradation of the bisphenol A resulted after 48 hours. Almost 60% of the carbon in bisphenol A was mineralized to carbon dioxide ($CO_2$) and 20% was associated with the bacterial cells. The remaining 20% of the carbon was recovered in the culture medium as soluble organic carbon after acidification to remove the $CO_2$. The following table shows the results obtained:

| CARBON MASS BALANCE FOR THE BIODEGRADATION OF BISPHENOL A BY BACTERIAL STRAIN MV1 | | | | |
|---|---|---|---|---|
| | SUBSTRATE (mMoles C) | PRODUCTS (mMoles C) | | |
| Culture Bottle | Carbon in Bisphenol A | Carbon Dioxide | Carbon Biomass | Carbon Aqueous | Total C Recovered |
| 1 | 2.00 | 1.23 | 0.37 | 0.40 | 2.00 |
| 2 | 2.00 | 1.21 | 0.40 | 0.42 | 2.03 |
|   | 2.00 | 1.04 | 0.40 | 0.43 | 1.87 |
| Average of 3 Bottles: | | 1.16 | 0.39 | 0.42 | 1.97 |
| Percent of Total Carbon | | 59% | 19.8% | 21.4% | 98.3% |

Above results show that 80% of the bisphenol A is degraded to $CO_2$ or converted to biomass. The remaining 20% of the bisphenol is biotransformed to soluble bisphenol A hydroxylation products.

EXAMPLE 2

In accordance with the procedure of example 1, there was added 5 volume % of a culture of strain MV1 grown on bisphenol A to one liter of PAS medium at 30° C. containing 5 grams of bisphenol A. The mixture was incubated for 4-5 days at 30° C. under aerobic conditions with limiting oxygen at a pH of 6.0-7.0. HPLC showed the formation of 2,2-bis(4-hydroxyphenyl)-1-propanol up to a concentration of 1.5 grams per liter.

EXAMPLE 3

Several bisphenol alkanes were individually incubated over a period of a few hours to several days at ambient temperatures with 1-2 grams wet weight of viable strain MV1 cells, which were grown on bisphenol A in accordance with the procedure of example 1. The following hydroxylation products were obtained.

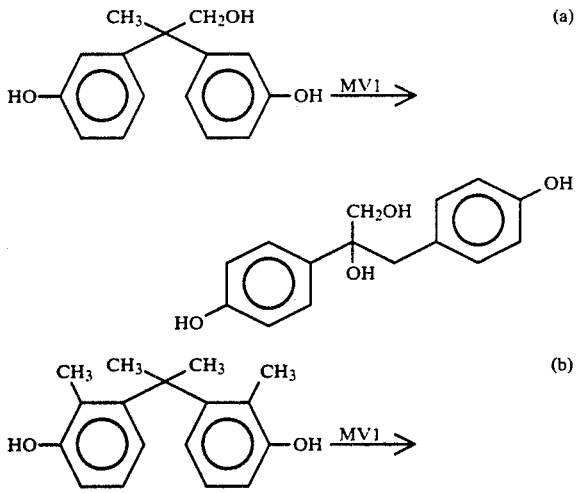

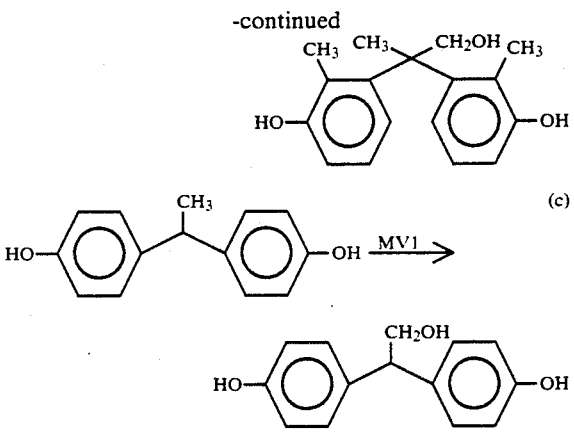

The above results show that the method of the present invention provides a procedure for making a variety of bisphenol alcohols which are useful compounds for making thermoplastics, such as polycarbonates and polyesters.

Although the above examples are directed to only few of the very many variables which can be employed in the practice of the present invention, it should be understood that the present invention is directed to a much broader variety of bisphenol alkanes and hydroxylation products obtained therefrom in accordance with the practice of the present invention.

What is claimed is:

1. A method for making hydroxylated bisphenol alkanes which comprises treating a bisphenol alkanes under aerobic conditions and at a pH in the range of 6 to 7 with an effective amount of a biologically pure culture of a gram negative, motile, rod-shaped bacterium NRRL-B-18737.

2. A method in accordance with claim 1, where the bisphenol alkane is bisphenol A.

3. Hydroxylated bishphenol alkanes made in accordance with the method of claim 1.

4. The compound 2,2-bis(4-hydroxyphenyl)-propanol.

5. The compound 2,3-bis(4-hydroxyphenyl)propane-1,2-diol.

* * * * *